(12) United States Patent
Sekiguchi et al.

(10) Patent No.: US 12,220,482 B2
(45) Date of Patent: Feb. 11, 2025

(54) LIPOSOME COMPOSITION AND METHOD FOR PRODUCING THE SAME

(71) Applicant: FUJIFILM Corporation, Tokyo (JP)

(72) Inventors: Takahiro Sekiguchi, Ashigarakami-gun (JP); Mikinaga Mori, Ashigarakami-gun (JP); Kentaro Numajiri, Ashigarakami-gun (JP); Hiroyuki Kitaoka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 556 days.

(21) Appl. No.: 17/140,502

(22) Filed: Jan. 4, 2021

(65) Prior Publication Data

US 2021/0128471 A1 May 6, 2021

Related U.S. Application Data

(63) Continuation of application No. 15/968,110, filed on May 1, 2018, now abandoned, which is a continuation
(Continued)

(30) Foreign Application Priority Data

Nov. 2, 2015 (JP) .................................. 2015-215767

(51) Int. Cl.
*A61K 9/127* (2006.01)
*A61K 31/7068* (2006.01)

(52) U.S. Cl.
CPC ............ *A61K 9/127* (2013.01); *A61K 9/1271* (2013.01); *A61K 9/1278* (2013.01); *A61K 31/7068* (2013.01)

(58) Field of Classification Search
CPC .... A61K 9/127; A61K 9/1271; A61K 9/1278; A61K 31/7068; A61P 35/00
See application file for complete search history.

(56) References Cited

U.S. PATENT DOCUMENTS 5,049,392 A 9/1991 Weiner et al.
5,094,854 A 3/1992 Ogawa et al.
(Continued)

FOREIGN PATENT DOCUMENTS

CA 2566 559 * 5/2014
EP 3138555 A1 3/2017
(Continued)

OTHER PUBLICATIONS

Office Action dated Jun. 8, 2022 issued by the European Patent Office in European Application No. 16862069.8.
(Continued)

*Primary Examiner* — Benjamin J Packard
*Assistant Examiner* — Lucy M Tien
(74) *Attorney, Agent, or Firm* — Sughrue Mion, PLLC

(57) ABSTRACT

An object of the present invention is to provide a liposome composition containing a liposome having an excellent leakage rate of a nucleic acid analog anticancer agent, and a method for producing the same. According to the present invention, there are provided a liposome composition containing a liposome which (1) contains a nucleic acid analog anticancer agent and in which (2) a content ratio of a lysophospholipid contained in a lipid forming the liposome with respect to a total amount of phospholipids other than the lysophospholipid contained in the lipid forming the liposome is 0.01 mol % to 5 mol % and (3) a nucleic acid analog anticancer agent/lipid ratio is 2 mass % to 10 mass %, and a method for producing the same.

6 Claims, 1 Drawing Sheet

Related U.S. Application Data of application No. PCT/JP2016/082417, filed on Nov. 1, 2016.

(56) References Cited

U.S. PATENT DOCUMENTS

| | | | |
|---|---|---|---|
| 5,153,000 A * | 10/1992 | Chikawa | A61K 8/556 264/4.1 |
| 5,393,530 A | 2/1995 | Schneider et al. | |
| 5,939,096 A | 8/1999 | Clerc et al. | |
| 5,993,850 A | 11/1999 | Sankaram et al. | |
| 6,726,925 B1 | 4/2004 | Needham | |
| 2003/0104046 A1 | 6/2003 | Patel | |
| 2003/0198664 A1 | 10/2003 | Sullivan et al. | |
| 2004/0265368 A1 | 12/2004 | Mayer et al. | |
| 2007/0082042 A1 * | 4/2007 | Park | A61P 17/16 424/450 |
| 2007/0286897 A1 | 12/2007 | Mayer et al. | |
| 2007/0298094 A1 | 12/2007 | Yoshino et al. | |
| 2008/0193511 A1 | 8/2008 | Massing | |
| 2008/0213183 A1 | 9/2008 | Bally et al. | |
| 2009/0047336 A1 | 2/2009 | Yang et al. | |
| 2010/0209364 A1 * | 8/2010 | Abe | A61K 8/31 424/59 |
| 2011/0200665 A1 | 8/2011 | Mei et al. | |
| 2012/0057178 A1 | 3/2012 | Kikuchi et al. | |
| 2012/0058178 A1 | 3/2012 | Kikuchi et al. | |
| 2012/0171283 A1 | 7/2012 | Hong et al. | |
| 2013/0230457 A1 * | 9/2013 | Reed | A61P 35/00 424/9.4 |
| 2014/0056968 A1 | 2/2014 | Gubernator et al. | |
| 2014/0294933 A1 | 10/2014 | Cha et al. | |
| 2015/0182460 A1 | 7/2015 | Hong et al. | |
| 2018/0243215 A1 | 8/2018 | Sekiguchi et al. | |
| 2019/0374468 A1 | 12/2019 | Smith et al. | |

FOREIGN PATENT DOCUMENTS

| | | |
|---|---|---|
| EP | 3138557 A1 | 3/2017 |
| EP | 3138558 A1 | 3/2017 |
| JP | 2-1404 A | 1/1990 |
| JP | 05-504150 A | 7/1993 |
| JP | 10-502667 A | 3/1998 |
| JP | 2000-302685 A | 10/2000 |
| JP | 2002-509866 A | 4/2002 |
| JP | 2006-522026 A | 9/2006 |
| JP | 2007-533670 A | 11/2007 |
| JP | 2016-117005 A | 6/2016 |
| WO | 2005/021012 A1 | 3/2005 |
| WO | 2012/055020 * | 5/2012 |
| WO | 2013123407 A1 | 8/2013 |
| WO | 2014/092858 A1 | 6/2014 |
| WO | 2015/166985 A1 | 11/2015 |
| WO | 2015/166986 A1 | 11/2015 |
| WO | 2015/166987 A1 | 11/2015 |
| WO | 2015/166988 A1 | 11/2015 |

OTHER PUBLICATIONS

R. Moog, et al., "Effect of nucleoside analogues and oligonucleotides on hydrolysis of liposomal phopholipids", International Journal of Pharmaceutics, 2000, pp. 43-53, vol. 206, No. 1-2.

"Cell-Kill-Kinetics," Cancer and Chemotherapy (1976) vol. 3; pp. 1103-1110.

Hongtao Xu, et al., "Development of High-Content Gemcitabine PEGylated Liposomes and Their Cytotoxicity on Drug-Resistant Pancreatic Tumour Cells", Pharm Res., 2014, vol. 31, No. 10.

Xu et al., "Development of High-Content Gemcitabine PEGylated Liposomes and Their Cytotoxicity on Drug-Resistant Pancreatic Tumour Cells," Pharm Res (2014) vol. 31; pp. 2583-2592.

Communication dated Aug. 8, 2018, from the European Patent Office in European application No. 6862069.8.

Office Action dated Apr. 23, 2019 issued by the Japanese Patent Office in Japanese application No. 2017-548770.

International Search Report dated Dec. 27, 2016 from the International Searching Authority in International Application No. PCT/JP2016/082417.

International Preliminary Report on Patentability dated May 8, 2018 from the International Bureau in International Application No. PCT/JP2016/082417.

Written Opinion of the International Searching Authority dated Dec. 27, 2016 in International Application No. PCT/JP2016/082417.

* cited by examiner

LIPOSOME COMPOSITION AND METHOD FOR PRODUCING THE SAME

CROSS-REFERENCE TO RELATED APPLICATIONS

This application is a continuation of application Ser. No. 15/968,110 filed May 1, 2018, which is a Continuation of PCT International Application No. PCT/JP2016/082417 filed on Nov. 1, 2016, which claims priority under 35 U.S.C § 119(a) to Japanese Patent Application No. 2015-215767 filed on Nov. 2, 2015. Each of the above application(s) is hereby expressly incorporated by reference, in its entirety, into the present application.

BACKGROUND OF THE INVENTION

1. Field of the Invention

The present invention relates to a liposome composition containing a liposome containing a nucleic acid analog anticancer agent, and a method for producing the same.

2. Description of the Related Art

As an anticancer agent, there is a drug of which attack on cancer cells is not affected by exposure time and a drug of which attack on cancer cells is significantly affected by exposure time as the anticancer agent is classified through descending classification (Cancer and Chemotherapy, 1976, Vol. 3, 1103-1110).

It is often studied that drugs are accumulated in cancerous tumors and exposed over a long period of time due to a liposome formulation. The liposome formulation is a formulation in which a drug is contained in a liposome formed of a lipid membrane.

In order to expose drugs to cancerous tumor over a long period of time, it is preferable to lower a drug leakage rate from liposome particles in blood.

A method for achieving a high drug encapsulation rate through distributing a mixture of liposomes and drugs in the liposomes while maintaining a constant temperature is disclosed in JP2002-509866A as a method for making a liposome contain a drug.

A remote loading method in which ammonium sulfate or the like is contained in a liposome and then the drug is encapsulated is disclosed in Pharmaceutical Research, 2014, 31, 12583-2592 as a method for making a liposome contain a drug.

SUMMARY OF THE INVENTION

Among anticancer agents, for example, an antimetabolite that inhibits synthesis of DNA attacks only a part of cells at a DNA synthesis phase. Therefore, in a case where an exposure time is short, effective cytocidal properties cannot be obtained. In a case where in vivo metabolism after administration of such a drug is fast, in many cases, sufficient exposure time in tumors cannot be obtained and an expected drug efficacy cannot be obtained. In addition, there is an administration method for exposing an anticancer agent at a dilute concentration for a long period of time through instillation in order to obtain sufficient exposure time. However, there is a problem in that the quality of life (QOL) is greatly impaired, for example, a problem of restraint of a patient during instillation.

In addition, according to the remote loading method disclosed in Pharmaceutical Research, 2014, 31, 12583-2592, an effect of improving the encapsulation rate cannot be obtained for drugs such as gemcitabine.

An object of the present invention is to provide a liposome composition containing a liposome having an excellent leakage rate of a nucleic acid analog anticancer agent, and a method for producing the same.

The present inventors have conducted extensive studies, and as a result, they have found that a liposome, in which a content ratio of a lysophospholipid contained in a lipid forming a liposome with respect to the total amount of a phospholipid other than the lysophospholipid contained in the lipid forming the liposome is 0.01 mol % to 5 mol % and a nucleic acid analog anticancer agent/lipid ratio is 2 mass % to 10 mass %, has an excellent leakage rate of a nucleic acid analog anticancer agent. In addition, they have also found that it is possible to produce a liposome composition containing the liposome having an excellent leakage rate of the nucleic acid analog anticancer agent by including a step of mixing a nucleic acid analog anticancer agent solution of which the temperature is kept at 40° C. to 50° C. with a solution in which an empty liposome is dispersed and a step of heating the mixture to a temperature of higher than or equal to 55° C., and have completed the present invention.

That is, the present invention provides the following.

[1] A liposome composition comprising: a liposome which (1) contains a nucleic acid analog anticancer agent and in which (2) a content ratio of a lysophospholipid contained in a lipid forming the liposome with respect to a total amount of phospholipids other than the lysophospholipid contained in the lipid forming the liposome is 0.01 mol % to 5 mol % and (3) a nucleic acid analog anticancer agent/lipid ratio is 2 mass % to 10 mass %.

[2] The liposome composition according to [1], in which the nucleic acid analog anticancer agent is gemcitabine or a salt thereof.

[3] The liposome composition according to [1] or [2], in which an average particle diameter of the liposome is 10 nm to 150 nm.

[4] The liposome composition according to any one of [1] to [3], in which the liposome having a particle diameter of greater than or equal to 200 nm is less than or equal to 1 mass %.

[5] The liposome composition according to any one of [1] to [4], in which an osmotic pressure of an inner aqueous phase of the liposome is 2 to 8 times an osmotic pressure of an outer aqueous phase of the liposome.

[6] A method for producing a liposome composition containing a liposome which (1) contains a nucleic acid analog anticancer agent and in which (2) a content ratio of a lysophospholipid contained in a lipid forming the liposome with respect to a total amount of phospholipids other than the lysophospholipid contained in the lipid forming the liposome is 0.01 mol % to 5 mol % and (3) a nucleic acid analog anticancer agent/lipid ratio is 2 mass % to 10 mass %, the method comprising: a step (a) of mixing a nucleic acid analog anticancer agent solution with a solution in which an empty liposome is dispersed; and a step (b) of heating the mixture to a temperature higher than or equal to 55° C.

[7] A method for producing a liposome composition containing a liposome which (1) contains a nucleic acid analog anticancer agent and in which (2) a content ratio of a lysophospholipid contained in a lipid forming the liposome with respect to a total amount of phospholipids other than the lysophospholipid contained in the lipid forming the liposome is 0.01 mol % to 5 mol % and (3) a nucleic acid analog anticancer agent/lipid ratio is 2 mass % to 10 mass %, the method comprising: a step (a) of mixing a nucleic acid analog anticancer agent solution with a solution in which an empty liposome is dispersed; a step (b) of heating the mixture to a temperature higher than or equal to 55° C.; and a step (c) of dissolving the nucleic acid analog anticancer agent solution at a pH of 1 to 5 before the step (a), in which the step (b) is a step of heating the mixture to a temperature higher than or equal to 55° C. at a pH 5.0 to 13.

[8] The method for producing a liposome composition according to [6] or [7], further comprising: a step (d) of lowering the temperature to 40° C. for longer than or equal to 5 minutes after the step (b) of heating the mixture to a temperature higher than or equal to 55° C.

[9] The method for producing a liposome composition according to any one of [6] to [8], further comprising: a step (e) of adjusting an osmotic pressure of an inner aqueous phase of the liposome to be 2 to 8 times an osmotic pressure of an outer aqueous phase of the liposome.

[10] The method for producing a liposome composition according to any one of [6] to [9], in which an empty liposome is prepared without being subjected to extrusion treatment.

The liposome contained in the liposome composition of the present invention has an excellent leakage rate of a nucleic acid analog anticancer agent.

In addition, it is possible to produce a liposome composition containing a liposome having an excellent leakage rate of a nucleic acid analog anticancer agent through a method for producing the liposome composition of the present invention.

DESCRIPTION OF THE PREFERRED EMBODIMENTS

Figure 1:
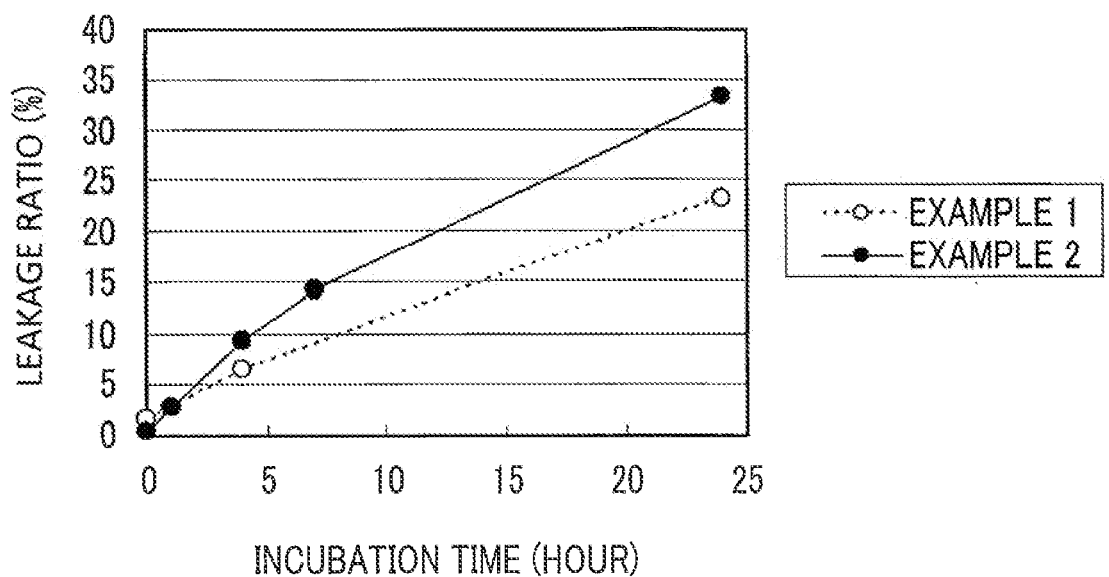
FIG. 1 is a graph showing a relationship between incubation time and a leakage ratio of gemcitabine in plasma.
Figure 2:
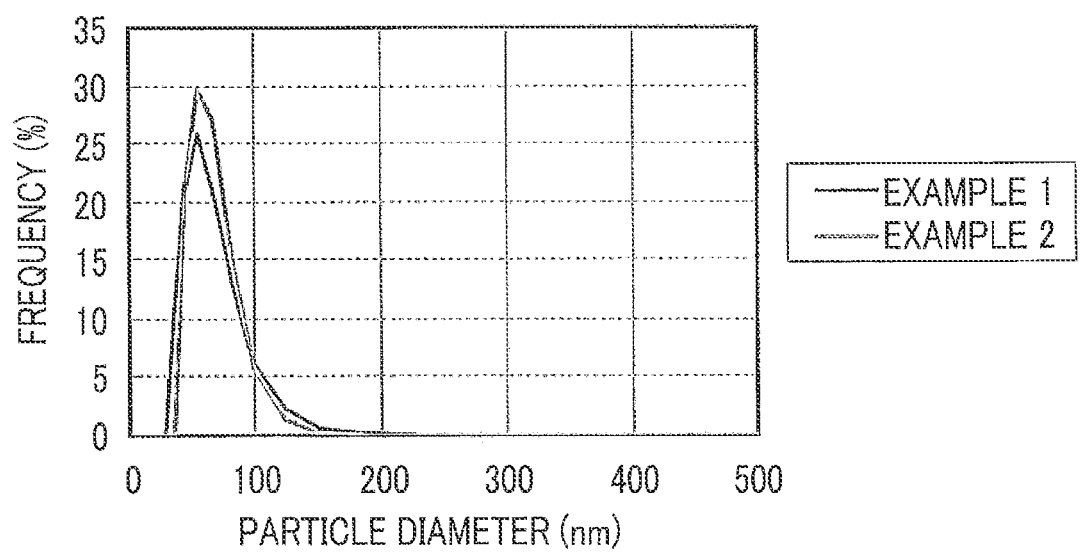
FIG. 2 is a graph showing a result of measurement of particle size distribution.

In the present specification, the numerical range represented by "to" indicates a range including numerical values denoted before and after "to" as a minimum value and a maximum value.

In the present invention, unless otherwise specified,% means a mass percentage.

In the present specification, the amount of each component in a composition means, unless otherwise specified, a total amount of a plurality of substances present in the composition in a case where the plurality of substances corresponding to each component are present in the composition.

The "nucleic acid analog anticancer agent/lipid ratio" means a mass ratio of a nucleic acid analog anticancer agent contained in a liposome to a lipid forming the liposome.

The "empty liposome" means a liposome containing no drug.

The "leakage" means that a drug contained in a liposome passes through a lipid membrane forming the liposome and is released to the outside of the liposome.

The "leakage rate" means an amount of a drug contained in a liposome which passes through a lipid membrane forming the liposome and is released to the outside of the liposome, per unit time.

It is important to maintain the state that a drug is contained in a liposome during production and storage of the liposome before administration, and it is preferable to control the leakage rate to a low level. On the other hand, in blood after the administration, it is preferable to allow the drug to leak out at a constant rate in order to expose the drug to a cancerous tumor.

"Retentivity in blood" means a property in which a drug in a state of being encapsulated in a liposome is present in blood in a target to which a liposome composition is administered.

The "average particle diameter of the liposome" means a volume average particle diameter of liposomes present in a liposome composition. The average particle diameter of liposomes contained in the liposome composition of the present invention is measured through a dynamic light scattering method. Examples of commercially available determination devices using dynamic light scattering include a concentrated particle analyzer FPAR-1000 (manufactured by OTSUKA ELECTRONICS Co., LTD.). NANO-TRAC UPA (manufactured by Nikkiso Co., Ltd.), and NANOSIZER (manufactured by Malvern Instruments Ltd.)

The "target" is a mammal, such as a human, a mouse, a monkey, or a domestic animal, requiring prevention or treatment of a tumor, and is preferably a human who requires prevention or treatment thereof.

Examples of the "tumor" include breast cancer, endometrial cancer, ovarian cancer, prostate cancer, lung cancer, stomach cancer (gastric adenocarcinoma), non-small-cell lung cancer, pancreatic cancer, head and neck squamous cell cancer, esophageal cancer, bladder cancer, melanoma, colorectal cancer, renal cell carcinoma, non-Hodgkin lymphoma, and urothelial cancer.

Hereinafter, the present invention will be described in detail.

(Liposome)

A liposome is a closed endoplasmic reticulum formed of a lipid bilayer membrane using a lipid and has an aqueous phase (inner aqueous phase) in a space of the closed endoplasmic reticulum. The inner aqueous phase contains water and the like. Liposomes usually exist in a state of being dispersed in an aqueous solution (outer aqueous phase) on the outside of the closed endoplasmic reticulum. A liposome may be a single lamella (also called a monolayer lamella or a unilamella, with a single layer structure of a bilayer membrane), or may be a multilayer lamella (also called a multilamella with a structure of multiple bilayer membranes having an onion shape in which each of the layers is partitioned by a watery layer). However, a liposome of a single lamella is preferable in the present invention from the viewpoints of safety and stability in medical use.

The form of the liposome is not particularly limited as long as it is a liposome capable of containing a drug. The "containing" means a form in which a drug is included in an inner aqueous phase and the membrane itself of the liposome. For example, a form in which a drug is contained in a closed space formed of a membrane, a form in which a drug is contained in a membrane itself, or a combination thereof may be used.

The average particle diameter of a liposome is preferably 10 nm to 150 nm, more preferably 20 nm to 110 nm, and still more preferably 30 nm to 90 nm.

It is preferable that a liposome has a spherical shape or a shape close thereto.

Components forming a lipid bilayer of a liposome are selected from lipids. A lipid dissolving in a mixed solvent of a water-soluble organic solvent and an ester-based organic solvent can be optionally used as the lipids. Examples of the lipids include phospholipids, lipids other than phospholipids, cholesterols, lysophospholipids, and derivatives thereof. These components may be formed of a single component or plural kinds of components.

Examples of phospholipids include natural or synthetic phospholipids such as phosphatidylcholine (lecithin), phosphatidylglycerol, phosphatidic acid, phosphatidylethanolamine, phosphatidylserine, phosphatidylinositol, sphingomyelin, and cardiolipin, or a substance hydrogenated thereto (for example, hydrogenated soybean phosphatidylcholine (HSPC)). Among these, hydrogenated phospholipids such as hydrogenated soybean phosphatidylcholine or sphingomyelin are preferable, and hydrogenated soybean phosphatidylcholine is more preferable. In the present invention. "phospholipids" also include phospholipid derivatives modified with phospholipids.

An example of lipids other than phospholipids include lipids not containing phosphoric acid. Examples thereof include glycerolipids having no phosphoric acid moiety in its molecule and sphingolipids having no phosphoric acid moiety in its molecule. In the present invention. "lipids other than phospholipids" also include derivatives of lipids other than phospholipids modified with lipids other than phospholipids.

In a case of a substance in which a compound having a basic functional group is bonded to a lipid, the lipid is called a cationized lipid. The cationized lipid can modify, for example, a membrane of a liposome, and therefore, it is possible to enhance the adhesiveness and the like to cells as target sites.

Examples of cholesterols include cholesterol, in which cyclopentahydrophenanthrene is a basic skeleton and a part or all of the carbon is hydrogenated, and a derivative thereof. An example thereof includes cholesterol. In a case where the average particle diameter is reduced to less than or equal to 100 nm, the curvature of a lipid membrane increases. Since distortion of membranes arranged in liposomes also increases, a water-soluble drug is more likely to leak out. It is effective to add cholesterol or the like in order to fill the distortion of membranes due to lipids (membrane stabilizing effect) as means to suppress the leakage.

It is expected that the addition of cholesterols to liposomes lowers the fluidity of membranes of the liposomes by, for example, filling the gap between the membranes of the liposomes. In general, it is desirable that cholesterols are usually contained in liposomes in an amount of about 50 mol % in the total (total lipid) mol of lipid components. However, in liposomes with a high osmotic pressure of an inner aqueous phase, the optimal range of the amount of cholesterols has not been known.

The content ratio of cholesterols with respect to the total amount of lipids forming the liposome according to the present invention is preferably 10 mol % to 35 mol %, more preferably 15 mol % to 25 mol %, and still more preferably 17 mol % to 21 mol %. By setting the content ratio of cholesterols with respect to the total amount of lipid components of the liposome to 10 mol % to 35 mol %, it is possible to obtain a liposome composition in which both excellent leakage rate and storage stability are achieved.

In addition to the above-described components, a hydrophilic polymer or the like for improving retentivity in blood, a fatty acid, diacetyl phosphate, or the like as a stabilizer of a membrane structure, and α-tocopherol or the like as an antioxidant may be added to a liposome. In the present invention, it is preferable not to use additives such as surfactants, for example, dispersion assistants which are not permitted for use in intravenous injection in medicinal use.

In the liposome according to the present invention, phospholipids, lipids other than phospholipids, cholesterols, or cholesterols are preferably modified with hydrophilic polymers, as phospholipids, lipids other than phospholipids, cholesterols, and derivatives thereof.

Examples of hydrophilic polymers include polyethylene glycols, polyglycerins, polypropylene glycols, polyvinyl alcohol, styrene-maleic acid anhydride alternating copolymers, polyvinyl pyrrolidone, and synthetic polyamino acid. The above-described hydrophilic polymers can be used alone or in combination of two or more thereof.

Among these, from the viewpoint of retentivity in blood of a formulation, polyethylene glycols, polyglycerins, and polypropylene glycols are preferable, and polyethylene glycol (PEG), polyglycerin (PG), and polypropylene glycol (PPG) are more preferable. Polyethylene glycol (PEG) is more preferable from the viewpoints of versatility and retentivity in blood.

The molecular weight of PEG is not particularly limited, but is 500 to 10,000 Dalton, preferably 1,000 to 7,000 Dalton. and more preferably 2,000 to 5,000 Dalton.

In the liposome according to the present invention, it is preferable to use a lipid modified with PEG (PEG-modified lipid) together with a main lipid contained in the liposome.

Examples of PEG-modified lipids include 1,2-distearoyl-3-phosphatidylethanolamine-PEG2000 (manufactured by NOF CORPORATION), 1,2-distearoyl-3-phosphatidylethanolamine-PEG5000 (manufactured by NOF CORPORATION) and 1,2-distearoyl-3-phosphatidylethanolamine-polyethylene glycol such as distearoyl glycerol-PEG2000 (manufactured by NOF CORPORATION). These PEG-modified lipids may be added such that 0.3 to 50 mass %, preferably 0.5 to 30 mass %, and more preferably 1 to 20 mass % is contained with respect to the total lipid amount.

In the liposome according to the present invention, a combination of hydrogenated soybean phosphatidylcholine (a lipid contained in the liposome), 1,2-distearoyl-3-phosphatidylethanolamine-polyethylene glycol (a lipid used together with a main lipid), and a lipid of cholesterol is preferable.

In the liposome according to the present invention, it is preferable not to contain an anionic polymer (polyanion).
(Lysophospholipid)

A lysophospholipid is a hydrolysate of a phospholipid and means a phospholipid having one acyl group.

Examples of lysophospholipids include lysophosphatidylcholine (lysolecithin), lysophosphatidylglycerol, lysophosphatidic acid, lysophosphatidylethanolamine, lysophosphatidylserine, lysophosphatidylinositol, lysosphingomyelin, and hydrogenated soybeanlysophosphatidylcholine.

In the present invention, the content ratio of the lysophospholipid contained in a lipid forming a liposome with respect to the total amount of phospholipids other than the lysophospholipid contained in the lipid forming the liposome is 0.01 mol % to 5 mol %, preferably 0.05 to 4 mol %, and more preferably 0.1 to 3 mol %. The leakage rate of a nucleic acid analog anticancer agent can be controlled by setting the content ratio of a lysophospholipid contained in a lipid forming a liposome to 0.01 mol % to 5 mol % with respect to the total amount of phospholipids other than the lysophospholipid contained in lipid forming the liposome.
(Nucleic Acid Analog Anticancer Agent)

The liposome according to the present invention contains a nucleic acid analog anticancer agent as a drug.

The nucleic acid analog anticancer agent is an anticancer agent that has a structure similar to that of a nucleic acid material such as purine base or pyrimidine base and exhibits its drug efficacy by being incorporated into a DNA chain.

Examples of nucleic acid analog anticancer agents include gemcitabine, cytarabine, thioguanine, enocitabine, capecitabine, nelarabine, decitabine, clofarabine, azacytidine, fludarabine, cladribine, 1-(2-deoxy-2-fluoro-4-thio-β-D-arabinofuranosyl) cytosine, or salts thereof.

Examples of the salt include salts of basic groups such as amino groups, and acidic groups such as hydroxyl groups and carboxyl groups, which are commonly known.

Examples of the salts of basic groups include salts of mineral acids such as hydrochloric acid, hydrobromic acid, nitric acid, and sulfuric acid; salts of organic carboxylic acids such as formic acid, acetic acid, citric acid, oxalic acid, fumaric acid, maleic acid, succinic acid, malic acid, tartaric acid, aspartic acid, and trichloroacetic acid and trifluoroacetic acid; and salts of sulfonic acids such as methanesulfonic acid, benzenesulfonic acid, p-toluenesulfonic acid, mesitylenesulfonic acid, and naphthalenesulfonic acid.

Examples of salts of acidic groups include salts of alkali metals such as sodium and potassium; salts of alkaline earth metals such as calcium and magnesium ammonium salts; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine. N-benzyl-β-phenethylamine, 1-ephenamine, and N,N'-dibenzylethylenediamine.

As the nucleic acid analog anticancer agent, gemcitabine or 1-(2-deoxy-2-fluoro-4-thio-β-D-arabinofuranosyl) cytosine or a salt thereof is preferable, and gemcitabine or a salt thereof is more preferable.

(Nucleic Acid Analog Anticancer Agent Contained in Liposome)

The drug (nucleic acid analog anticancer agent) contained in the liposome according to the present invention is present in a dissolved state in an inner aqueous phase of the liposome. Here, the dissolved state is regarded as a condition in which a drug is contained in a dissolved state in a case where the amount of the drug loaded with respect to the volume of the liposome is less than or equal to saturated solubility of the drug in the composition liquid of the inner aqueous phase. In addition, in a case where drug crystal is not observed with Cryo-TEM even at greater than or equal to saturated solubility, or in a case where no diffraction pattern due to crystal lattice is observed through XRD measurement, it is regarded that most of the drug contained in the liposome dissolves and is contained in a dissolved state. In this case, it is estimated that dissolution enhancement due to physicochemical environment created by the lipid membrane or partial incorporation of a drug into the lipid membrane occurs. In addition, even in a case where a drug having a high water solubility is contained through a method for encapsulating the drug by forming a solid substance within a liposome, the drug does not enter the dissolved state as referred to in the present invention.

The nucleic acid analog anticancer agent contained in a dissolved state is preferably one having a solubility of greater than or equal to 1 mg/ml with respect to water and more preferably having a solubility of greater than or equal to 10 mg/m with respect to water. Specifically, gemcitabine is preferable.

The content of the nucleic acid analog anticancer agent contained in the liposome is preferably 0.1 to 2.0 mg/ml and more preferably 0.2 to 1.0 mg/ml with respect to the liposome composition.

(Nucleic Acid Analog Anticancer Agent/Lipid Ratio)

The nucleic acid analog anticancer agent/lipid ratio of the liposome according to the present invention is 2 mass % to 10 mass %, preferably 2.5 mass % to 10 mass %, and more preferably 3 mass % to 10 mass %. By setting the nucleic acid analog anticancer agent/lipid ratio to 2 mass % to 10 mass %, it is possible to suppress hyperlipidemia and fatty liver due to lipids while controlling the leakage rate within a preferable range. The lipids in the nucleic acid analog anticancer agent/lipid ratio mean all the lipids forming a liposome, and the lipids also include lysophospholipids.

(Liposome Composition)

The liposome composition according to the present invention can contain liposomes containing a nucleic acid analog anticancer agent and an aqueous solution in which the liposomes are dispersed.

From the viewpoints of filter filtration suitability suitable for commercial production and tumor accumulation properties due to an EPR effect, the liposome composition of the present invention preferably has less than or equal to 1 mass % of a liposome having a particle diameter of greater than or equal to 200 nm, more preferably less than or equal to 0.5 mass %, and still more preferably less than or equal to 0.1 mass %

In the liposome composition according to the present invention, the osmotic pressure of the inner aqueous phase of the liposome is preferably 2 to 8 times, more preferably 2.5 to 6 times, and still more preferably 3 to 5 times the osmotic pressure of the outer aqueous phase of the liposome. By setting the osmotic pressure of the inner aqueous phase of the liposome to 2 to 8 times the osmotic pressure of the outer aqueous phase of the liposome, it is possible to achieve both excellent drug leakage rate and storage stability.

It is possible to appropriately add an aqueous solvent, an additive, and the like to the liposome composition. The liposome composition may contain at least one of a pharmaceutically acceptable isotonic agent, a stabilizer, an antioxidant, and a pH adjuster in relation to the administration route.

The isotonic agents are not particularly limited, but examples thereof include inorganic salts such as sodium chloride potassium chloride, sodium hydrogen phosphate, sodium dihydrogen phosphate, and potassium dihydrogen phosphate, polyols such as glycerol, mannitol, and sorbitol, and saccharides such as glucose, fructose, lactose, or sucrose.

The stabilizer is not particularly limited, but examples thereof include saccharides such as glycerol, mannitol, sorbitol, lactose, or sucrose.

The antioxidants are not particularly limited, but examples thereof include ascorbic acid, uric acid, tocopherol homologues (for example, vitamin E or four isomers of tocopherol α, β, γ, and δ) cysteine, and ethylenediaminetetraacetic acid (EDTA). The above-described stabilizer and antioxidant can be used alone or in combination of two or more thereof.

Examples of pH adjusters include sodium hydroxide, citric acid, acetic acid, triethanolamine, sodium hydrogen phosphate, sodium dihydrogen phosphate, and potassium hydrogen phosphate.

The liposome composition may contain a pharmaceutically acceptable organic solvent, collagen, polyvinyl alcohol, polyvinyl pyrrolidone, carboxyvinyl polymer, sodium carboxymethyl cellulose, sodium polyacrylate, sodium alginate, water soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, PBS, sodium chloride, saccharides, an in vivo degradable polymer, a serum-free medium, and an additive which is acceptable as a pharmaceutical additive.

In particular, the liposome composition according to the present invention preferably contains ammonium sulfate. L-histidine, purified white sugar, sodium hydroxide, or hydrochloric acid.

A container to be filled with the liposome composition is not particularly limited, but it is preferably a material having low oxygen permeability. An example thereof includes a bag using a laminate film having a plastic container, a glass container, an aluminum foil, an aluminum vapor deposition film, an aluminum oxide vapor deposition film, a silicon oxide vapor deposition film, polyvinyl alcohol, an ethylene vinyl alcohol copolymer, polyethylene terephthalate, polyethylene naphthalate, polyvinylidene chloride, and the like as a gas barrier layer. It is possible to shield light by employing a bag as necessary in which colored glass, aluminum foil, aluminum vapor deposition film, or the like is used.

In the container filled with the liposome composition, it is preferable to replace gas in a container space portion and in a drug solution with an inert gas such as nitrogen in order to prevent oxidation caused by oxygen present in the space portion in the container. For example, nitrogen bubbling of an injection solution and filling of the container in a nitrogen atmosphere can be performed.

Parenteral administration is preferable as an administration route of the liposome composition. Examples thereof include intravenous injection such as instillation, intramuscular injection, intraperitoneal injection, subcutaneous injection, intraocular injection, and intrathecal injection. An example of the administration method includes administration using a syringe or through instillation.

The dosage and the number of times of administration of the drug contained in the liposome composition are selected within a range of 0.01 mg/kg to 100 mg/kg per day. However, the dosage of the liposome composition of the present invention is not limited.

Cancer for which the liposome composition of the present invention can be effectively used is not particularly limited as long as they are carcinomas and sarcomas in which a taxane antitumor agent is used. However, examples thereof include breast cancer, endometrial cancer, ovarian cancer, prostate cancer, lung cancer, stomach cancer (gastric adenocarcinoma), non-small-cell lung cancer, pancreatic cancer, head and neck squamous cell cancer, esophageal cancer, bladder cancer, melanoma, colorectal cancer, renal cell carcinoma, non-Hodgkin lymphoma, and urothelial cancer, and pancreatic cancer is preferable.

(Leakage Rate in Blood)

In the liposome composition according to the present invention, the leakage rate of a drug in blood is preferably 10 mass %/24 hr to 70 mass %/24 hr, more preferably 20 mass %/24 hr to 60 mass %/24 hr. and still more preferably 20 mass %/24 hr to 50 mass %/24 hr.

Since the leakage rate in blood depends on the temperature, it is preferable to measure the release rate under a constant temperature condition. For example, in a case of humans, the temperature is not particularly limited, but it is preferable to measure the leakage rate within a range of body temperature (35° C. to 38° C.).

In cases where a drug contained in a liposome is a nucleic acid analog anticancer agent and the leakage rate of the drug in blood is less than 15 mass %/24 hr. sufficient exposure time of the nucleic acid analog anticancer agent in the body cannot be obtained, and in many cases, the expected drug efficacy cannot be obtained. Depending on the circumstances, liposomes containing the nucleic acid analog anticancer agent remain in the body for an unnecessarily long period of time, and therefore, in some cases, unexpected toxicity may be exhibited due to accumulation of the liposomes in the tissue such as the skin in which the liposomes are hardly distributed normally. In addition, in a case where the leakage rate in blood is greater than 70 mass %/24 hr. the amount of drug to be exposed per unit time increases. Therefore, the maximum blood concentration increases, thereby increasing the toxicity. In addition, the retentivity in blood decreases due to a leaking drug which is distributed in tissues other than a tumor site and undergoes rapid metabolism.

The method for measuring the leakage rate in blood is not particularly limited. However, after administering the drug to a target mammal, model system, or the like, blood, plasma, or the like is collected from the mammal or the model system every unit time, and pretreatment or the like is performed as necessary. Moreover, the target drug can be measured through a method such as liquid high-speed chromatography or mass spectrometry.

(Method for Producing Liposome Composition)

The method for producing a liposome composition of the present invention is a method for producing a liposome composition containing a liposome which (1) contains a nucleic acid analog anticancer agent and in which (2) a content ratio of a lysophospholipid contained in a lipid forming the liposome with respect to a total amount of phospholipids other than the lysophospholipid contained in the lipid forming the liposome is 0.01 mol % to 5 mol % and (3) a nucleic acid analog anticancer agent/lipid ratio is 2 mass % to 10 mass %, the method including: a step (a) of mixing a nucleic acid analog anticancer agent solution (preferably a nucleic acid analog anticancer agent solution of which the temperature is kept at 40° C. to 50° C.) with a solution in which an empty liposome is dispersed; and a step (b) of heating the mixture to a temperature higher than or equal to 55° C.

The method for producing a liposome composition of the present invention can include a step (f) of emulsifying a lipid dissolved in an organic solvent to form an empty liposome without undergoing a drying and solidifying step before the step (a) of mixing a nucleic acid analog anticancer agent solution (preferably a nucleic acid analog anticancer agent solution of which the temperature is kept at 40° C. to 50° C.) with a solution in which an empty liposome is dispersed.

The method for producing the liposome composition of the present invention can further include a step (e) of adjusting an osmotic pressure of an inner aqueous phase of the liposome to be 2 to 8 times an osmotic pressure of an outer aqueous phase of the liposome.

The method for producing a liposome composition may include other steps such as an evaporation step of evaporating the organic solvent used in the emulsification step, aseptic filtration, and aseptic filling as necessary.

(Emulsification Step)

In the emulsification step, an aqueous phase can be mixed with an oil phase in which at least one kind of lipid is dissolved in an organic solvent, and the aqueous solution containing the lipid can be stirred and emulsified. By performing the mixing, stirring, and emulsifying of the aqueous phase and the oil phase in which the lipid is dissolved in the organic solvent, an emulsion in which the oil phase and the aqueous phase are emulsified in an O/W type is prepared. After mixing, a part or all of the organic solvent derived from the oil phase is removed by an evaporation step to be described below to form a liposome. Alternately, a part or all of the organic solvent in the oil phase evaporates in the process of the stirring and the emulsifying to form a liposome.

As the stirring method, ultrasonic wave or mechanical shear force is used for particle miniaturization. In addition, in order to make the particle diameter uniform, an extruder treatment or a microfluidizer treatment can be performed through a filter having a constant pore diameter. Using an extruder or the like, a secondarily formed multivesicular liposome can be released to form a univesicular liposome. In the present invention, it is preferable to use an empty liposome in the next step without being subjected to extrusion treatment from the viewpoint of simplifying the production step.

In the present invention, the average particle diameter of liposomes to be prepared can be controlled by optionally selecting the speed and time of stirring. From the viewpoint of obtaining liposomes having safety and stability, it is preferable to apply shearing to an aqueous solution containing lipids at a circumferential speed of higher than or equal to 20 m/sec. The shearing is not limited. However, specifically, it is preferable to apply shearing at a circumferential speed of 20 m/sec to 35 m/sec and more preferable to apply shearing at a circumferential speed of 23 m/sec to 30 m/sec.

The emulsification step is not limited as long as it is a step of emulsification, but is preferably a step of applying high shearing and forming fine particles in an emulsification step in which an organic solvent is contained. A liposome can be formed by evaporating (removing the solvent) the organic solvent used in the emulsification step as necessary.

The liquid temperature in the emulsification step in a case of producing the liposome can be appropriately controlled. The liquid temperature at the time of mixing an oil phase with an aqueous phase is preferably higher than or equal to a phase transition temperature of a lipid to be used. For example, in a case where a lipid having a phase transition temperature of 35° C. to 40° C. is used, liquid temperature is preferably 35° C. to 70° C.

(Oil Phase)

A mixed solvent of a water-soluble organic solvent and an ester-based organic solvent is used as an organic solvent used as an oil phase. In the present invention, it is preferable not to substantially use organic solvents such as chloroform, methylene chloride, hexane, cyclohexane, and the like as organic solvents, and it is more preferable not to use these organic solvents at all.

The water-soluble organic solvent is preferably an organic solvent having a property of being optionally mixed with water. Examples of the water-soluble organic solvent include alcohols such as methanol, ethanol, n-propanol, isopropanol, n-butanol, isobutanol, and t-butanol, glycols such as glycerin, ethylene glycol, and propylene glycol, and polyalkylene glycols such as polyethylene glycol. Among these, alcohols are preferable. As alcohols, at least one selected from ethanol, methanol, 2-propanol, and t-butanol is preferable, at least one selected from ethanol, 2-propanol, and t-butanol is more preferable, and ethanol is still more preferable.

The ester-based organic solvent is preferably an ester obtained from a reaction between an organic acid and alcohol. Examples of the ester-based organic solvent include ethyl acetate, methyl acetate, isopropyl acetate, t-butyl acetate, and methyl propionate. At least one selected from ethyl acetate, isopropyl acetate, and methyl propionate is preferable, and ethyl acetate is more preferable.

The mixing ratio of the water-soluble organic solvent and the ester-based organic solvent can be set to, by mass ratio, for example, 90:10 to 30:70, and is preferably 80:20 to 40:60 and more preferably 80:20 to 70:30. The mixed solvent of the water-soluble organic solvent and the ester-based organic solvent may further contain a aqueous solvent such as water or a buffer solution. The aqueous solvent can be added within a range of, for example, 1 to 30 mass %. The pH of the mixed solvent can be set, for example, to 3 to 10, and is preferably 4 to 9. The ester-based organic solvent may contain physiologically active substances such as various drugs soluble in these solvents.

In a case where ethanol is used as the water-soluble organic solvent and ethyl acetate is used as the ester-based organic solvent, the mixing ratio of ethanol to ethyl acetate can be set, for example, to 80:20 to 70:30 by mass ratio.

The concentration of the lipid is not particularly limited and can be appropriately adjusted. However, in a solution using a mixed solution of a water-soluble organic solvent and an ester-based organic solvent, as a solvent, the concentration can be set to 40 g/L to 250 g/L. and is preferably 100 g/L to 200 g/L.

(Aqueous Phase)

The aqueous phase means an outer aqueous phase and an inner aqueous phase.

The outer aqueous phase in the present invention means an aqueous solution in which liposomes are dispersed. In a case of injections, for example, a solution occupying the outside of liposomes of a liposome dispersion liquid stored by being packaged in a vial or a prefilled syringe becomes an outer aqueous phase. In addition, regarding a solution dispersed at the time of use during administration using an attached liquid for dispersion or other dissolution liquid, a solution occupying the outside of liposomes of a liposome dispersion liquid becomes an outer aqueous phase.

The inner aqueous phase in the present invention means an aqueous phase in a closed endoplasmic reticulum separated by a lipid bilayer membrane of a liposome.

In a case of producing liposomes, water (distilled water, water for injection, or the like), physiological saline, various buffer solutions or aqueous solutions of saccharides, and a mixture thereof (aqueous solvent) are preferably used as aqueous solutions (outer aqueous phases) in which liposomes are dispersed. The buffer solution is not limited to an organic type and an inorganic type. However, a buffer solution having a buffering action in the vicinity of the hydrogen ion concentration close to a body fluid is suitably used, and examples thereof include a phosphate buffer solution, a Tris buffer solution, a citrate buffer solution, an acetate buffer solution, and Good's buffer solution. The pH of an aqueous phase can be set, for example, to 5 to 9, and is preferably 7 to 8. It is preferable to use a phosphate buffer solution (for example, pH=7.4) as the aqueous solution (outer aqueous phase) in which liposomes are dispersed. In a case of producing liposomes, an inner aqueous phase of liposomes may be an aqueous solution in which liposomes are dispersed, or water, physiological saline, various buffer solutions or aqueous solutions of saccharides, and a mixture thereof. Water used as an outer aqueous phase or an inner aqueous phase preferably does not contain impurities (such as dust and chemical substances).

The physiological saline means an inorganic salt solution adjusted so as to be isotonic with a human body, and may have a buffering function. Examples of the physiological saline include saline containing 0.9 w/v % sodium chloride, phosphate-buffered physiological saline (hereinafter, also referred to as PBS) and Tris-buffered physiological saline.

An aqueous solution containing liposomes prepared through the emulsification step is subjected to after-treatment through methods such as centrifugal separation, ultrafiltration, dialysis, gel filtration, or freeze-drying in order to remove components not contained in the liposomes or adjust the concentration or osmotic pressure.

(Extrusion Treatment)

The obtained liposomes can have a uniform particle diameter through a dialysis method, a filtration method, an extrusion treatment, or the like.

The extrusion treatment means a step of applying a physical shear force by passing liposomes through a filter having pores for atomization. In the case of passing the liposomes through the filter, the atomization can be rapidly performed by keeping the temperature of a liposome dispersion liquid and the filter at a temperature higher than or equal to the phase transition temperature of membranes forming the liposomes.

In the production method of the present invention, from the viewpoint of suitability for commercial production, there is a difficulty in manufacture suitability (in particular, clogging and the like), and therefore, it is preferable that empty liposomes are prepared without being subjected to extrusion treatment at high cost.

(Step of Making Liposome Contain Nucleic Acid Analog Anticancer Agent) In the method for producing a liposome composition of the present invention, it is possible to make a liposome contain a nucleic acid analog anticancer agent through a step (a) of mixing a nucleic acid analog anticancer agent solution of which the temperature is kept at 40° C. to 50° C. with a solution in which an empty liposome is dispersed and a step (b) of heating the mixture to a temperature of higher than or equal to 55° C.

The liposome having an excellent leakage rate is obtained through the steps.

The method for producing a liposome composition of the present invention includes a step (c) of dissolving the nucleic acid analog anticancer agent solution at a pH of 1 to 5 before the step (a) of mixing a nucleic acid analog anticancer agent solution (preferably a nucleic acid analog anticancer agent solution of which the temperature is kept at 40° C. to 50° C.) with a solution in which an empty liposome is dispersed. It is preferable that the step (b) of heating the mixture to a temperature of higher than or equal to 55° C. is a step of heating the mixture to a temperature higher than or equal to 55° C. at a pH 5.0 to 13, preferably at a pH of 6.0 to 9.0, and more preferably at a pH of 6.5 to 8.0.

By dissolving the nucleic acid analog anticancer agent solution at a pH of 1 to 5, it is possible to dissolve the nucleic acid analog anticancer agent at a high concentration. On the other hand, in a case where the nucleic acid analog anticancer agent is contained in a liposome in a range of a pH of 1 to 5, lipids of the liposome are easily decomposed, and lysophospholipids and the like increase. In addition, analogs of the nucleic acid analog anticancer agents also increase. For this reason, it is possible to suppress the increase of lysophospholipids and analogs of a nucleic acid analog anticancer agent by carrying out the step of making a liposome contain the nucleic acid analog anticancer agent at a pH of 5.0 to 13, preferably at a pH of 6.0 to 9.0, and more preferably at a pH of 6.5 to 8.0.

The method for producing a liposome composition of the present invention preferably further includes a step (d) of lowering the temperature to 40° C. for longer than or equal to 5 minutes after the step (b) of heating the mixture to a temperature higher than or equal to 55° C.

The temperature is lowered to 40° C. for longer than or equal to 5 minutes in the step of lowering the temperature. The temperature is preferably lowered to 40° C. for longer than or equal to 10 minutes and more preferably for longer than or equal to 15 minutes.

It is possible to control the leakage rate of a drug in blood and further to keep the leakage rate in blood constant by including the step of lowering the temperature to 40° C. for longer than or equal to 5 minutes. Obtaining a constant leakage rate in blood by controlling only the temperature lowering rate is an unexpected effect. It is presumed that this is because the liposome membrane becomes homogeneous by lowering the temperature slowly.

(Osmotic Pressure Adjusting Step)

It is preferable that the method for producing the liposome composition of the present invention further includes a step (e) of adjusting an osmotic pressure of an inner aqueous phase of the liposome to be 2 to 8 times an osmotic pressure of an outer aqueous phase of the liposome.

In the step of adjusting the osmotic pressure, the osmotic pressure of an inner aqueous phase of a liposome is adjusted to be 2 to 8 times the osmotic pressure of an outer aqueous phase of the liposome. The osmotic pressure of the inner aqueous phase of the liposome is preferably adjusted to 2.5 to 6 times the osmotic pressure of the outer aqueous phase of the liposome and more preferably 3 to 5 times the osmotic pressure of the external aqueous phase of the liposome.

The leakage rate can be controlled by adjusting the osmotic pressure of an inner and an outer aqueous phase of a liposome. The step of adjusting the osmotic pressure is not particularly limited, but an example thereof includes dialysis. In the method for producing a liposome composition of the present invention, it is preferable to simultaneously perform a step of containing a nucleic acid analog anticancer agent in a liposome and the step of adjusting the osmotic pressure from the viewpoint of production efficiency.

Solutes of an outer aqueous phase and an inner aqueous phase in a liquid obtained after the step of making a liposome contain a nucleic acid analog anticancer agent are homogenized, and the osmotic pressure at that time can be defined as an osmotic pressure of the inner aqueous phase of the liposome composition to be obtained. However, in the subsequent step of adjusting osmotic pressure performed through dialysis of an outer aqueous phase, a heating operation is limited to a case where a solute of an inner aqueous phase is sufficiently held, for example, by controlling the temperature to be lower than or equal to the phase transition temperature of a lipid. The osmotic pressure of an outer aqueous phase can also be defined as an osmotic pressure of a dialysis solution used in the final dialysis step. However, this is limited to a case where it is possible to sufficiently perform replacement with the dialysis solution. In addition, regarding the obtained liquid of a liposome composition, it is also possible to obtain the osmotic pressures of an inner aqueous phase and an outer aqueous phase by quantitatively determining the composition concentration of a solute of the outer aqueous phase and the composition concentration of a solute of the inner aqueous phase through centrifugal separation or ultrafiltration, and measuring the osmotic pressure of the composition liquid.

The osmotic pressure may be measured according to an osmometry method disclosed in the Japanese Pharmacopoeia, 16th Edition. More specifically, the osmolality can be obtained by measuring the freezing point descending degree of water. In addition, the freezing point descending degree of water is defined by the solute molarity, and the osmolality can also be obtained from the solute molarity.

The osmotic pressure of the outer aqueous phase exerts an essential effect on the living body during administration. In a case where the osmotic pressure of the outer aqueous phase is far from osmotic pressure of body fluid, hemolysis or pain is caused due to movement of water in each tissue. Accordingly, the osmotic pressure of the outer aqueous phase is preferably 200 mOsmol/L to 400 mOsmol/L, more preferably 250 mOsmol/L to 350 mOsmol/L, and still more preferably isotonic with body fluid.

(Evaporation Step)

An evaporation step may be provided in the method for producing a liposome composition as necessary. In the evaporation step, an organic solvent is evaporated from an aqueous solution containing the liposomes obtained in the emulsification step. In the present invention, the evaporation step includes at least a step of forcibly removing a part or all of the organic solvent derived from an oil phase as an evaporation step and a step of naturally evaporating a part or all of the organic solvent in an oil phase in the process of stirring and emulsifying.

The method for evaporating an organic solvent in the evaporation step is not particularly limited. However, for example, at least one of a step of evaporating an organic solvent through heating, a step of being left to stand or continuing gentle stirring after the emulsification, and a step of performing vacuum degassing may be performed.

In the step of evaporating an organic solvent, it is preferable to set the concentration of the organic solvent contained in an aqueous solution containing liposomes to less than or equal to 15 mass % within 30 minutes from the start of the step of evaporating an organic solvent.

(Aseptic Filtration)

The liposome composition is preferably subjected to aseptic filtration. As a filtration method, unnecessary substances can be removed from an aqueous solution containing liposomes using a hollow fiber membrane, a reverse osmosis membrane, a membrane filter, or the like. In the present invention, the filtration is preferably performed using a filter having a sterilizable pore diameter (preferably a 0.2 μm filtration sterilization filter).

In order to prevent the influence on the average particle diameter due to deformation of liposomes, it is preferable to carry out the aseptic filtration step and the aseptic filling step, to be described below, at a temperature lower than or equal to the phase transition temperature of a lipid forming the liposome. For example, in a case where the phase transition temperature of the lipid is around 50° C., about 0° C. to 40° C. is preferable and about 5° C. to 30° C. is more specifically preferable.

(Aseptic Filling)

The liposome composition obtained after the aseptic filtration is preferably subjected to aseptic filling for medical use. A well-known aseptic filling method can be applied. It is possible to prepare a suitable liposome composition for medical use by aseptically filling a container therewith.

EXAMPLES

Hereinafter, the present invention will be described in detail using examples. However, the present invention is not limited to the examples.

The osmotic pressure was calculated from the solute molarity.

For the average particle diameter and particle size distribution, a sample was diluted 33 times the mass of the sample with phosphate-buffered physiological saline, and the volume average particle diameter and volume distribution of particle diameters were measured through a dynamic light scattering method using FPAR-1000AS (manufactured by OTSUKA ELECTRONICS Co., LTD.)

Gemcitabine contained in a liposome was quantitatively determined through liquid chromatography/ultraviolet-visible absorbance detection. Measurement conditions are shown below.

Measurement wavelength: 272 nm

Column: Waters Atlantis T3φ, 4.6 mm×150 mm, 5 μm (manufactured by Waters)

Column temperature: Constant temperature around 40° C.

Both mobile phases A and B were water-methanol-trifluoroacetic acid mixed solutions, and the mobile phases were feed by changing the mixing ratio of the mobile phase A to the mobile phase B to control the concentration gradient.

Mobile phase A: Methanol/water volume ratio of 5/95, 0.1% trifluoroacetic acid

Mobile phase B: Methanol/water volume ratio of 25/75, 0.1% trifluoroacetic acid

Flow rate: 1.0 mL/min

Injection amount: 10 μL

Liquid temperature during sample injection: Constant temperature around 25° C.

Lipids constituting a liposome were quantitatively determined through liquid chromatography/CAD detection. Measurement conditions are shown below.

Column: Waters Xbridge, 4.6 mm×250 mm, 5 μm (manufactured by Waters)

Column temperature: Constant temperature around 40° C.

A 7 mM ammonium acetate methanol solution was used for both mobile phases A and B.

Flow rate: 1.0 mL/min

Injection amount: 10 μL

Liquid temperature during sample injection: Constant temperature around 25° C.

Lysophospholipids contained in lipids forming a liposome were quantitatively determined through the following method.

10 mg of C17 lysophosphatidyl choline was weighed in a 10 mL volumetric flask and diluted with ethanol, which was further diluted 50 times to prepare an internal standard solution.

20 μL of a liposome composition was weighed and diluted 20 times by adding 380 μL of ethanol thereto. 400 μL of the internal standard solution was added to and mixed with this solution to prepare a measurement sample which was then quantitatively determined through liquid chromatography mass spectrometry. Measurement conditions are shown below.

Column: ACQUTY UPLC BEH C18, 2.1 mm×50 mm. 1.7 μm (manufactured by Waters)

Column temperature: Constant temperature around 40° C.

Mobile phase: The concentration gradient was controlled by changing the mixing ratio of a mobile phase A to a mobile phase B.

Mobile phase A: Water/methanol volume ratio of 20/80

Mobile phase B: Methanol

Flow rate: 0.5 mL/min

Injection amount: 5 μL

Liquid temperature during sample injection: Constant temperature around 25° C.

Example 1 a) Preparation of Oil Phase 16.6 g, 2.0 g. and 4.3 g of hydrogenated soybean phosphatidylcholine, cholesterol, and an N-(carbonyl-methoxypolyethylene glycol 2000)-1,2-distearoyl-sn-glycero-3-phosphoethanolamine sodium salt (hereinafter, also referred to as DSPE-PEG) were respectively taken so as to have a molar ratio of 76/19/5. Subsequently, 405 mL of an organic solvent (ethanol/ethyl acetate=3/1) was added thereto and lipids are dissolved at a heated temperature of 70° C. to obtain an oil phase.

b) Preparation of Aqueous Phase

A 4 mM phosphate buffer solution (pH of 7.61) was prepared and used as an aqueous phase.

c) Preparation of Drug Non-Contained Liposome

The aqueous phase was heated to 70° C. and the oil phase was added thereto so that the volume ratio of water phase/oil phase=8/3, and then, the aqueous phase and the oil phase were mixed using a rotary stirring emulsifier (M Technique Co., Ltd.) at a circumferential speed of 20 m/s at 13.000 rpm for 30 minutes. Thereafter, the organic solvent and water were evaporated by supplying nitrogen while heating the mixture to higher than or equal to a phase transition temperature, and the mixture was concentrated so as to became a volume of about 1/10 of the volume before emulsification, to obtain a drug non-contained liposome. The average particle diameter at this time was 67.5 nm.

d) Preparation of Drug-Contained Liposome

Gemcitabine hydrochloride was used as a drug. Gemcitabine hydrochloride was purchased from TEVA.

1) Preparation of PBS (10×)

81.63 g of sodium chloride, 29.01 g of disodium hydrogen phosphate dodecahydrate, and 2.29 g of sodium dihydrogen phosphate dihydrate were dissolved in 948 g of water for injection to prepare PBS (10×).

2) Preparation of Drug Loading Solution 3.26 g of gemcitabine hydrochloride, 13.59 g of PBS, 19.05 g of water for injection of Japanese Pharmacopoeia, and 0.68 mL of 8 M sodium hydroxide were mixed with each other and were dissolved at 70° C. to prepare a drug solution. The temperature of 15.7 mL of this drug solution was kept at 45° C. 16.0 mL of a drug non-encapsulated liposome and 0.32 mL of 8 M sodium hydroxide were added thereto and mixed with each other. The osmotic pressure of the solution is 1.039 mOsm/L, which is an osmotic pressure of an inner aqueous phase of the obtained liposome. Next, the solution was heated at 70° C. for 10 minutes, and then, cooled to 40° C. over 30 minutes and diluted with a 1,016 mM sucrose/37 mM histidine solution. After the dilution, the solutions were combined into one solution to prepare a drug loading solution. A 275 mM sucrose/10 mM histidine aqueous solution was prepared as an obtained dialysis solution of the liposome composition through dialysis. The osmotic pressure obtained from the solute molarity of this solution was 285 mOsm/L. Dialysis was performed at room temperature using this dialysis solution, each solute and non-encapsulated gemcitabine hydrochloride present in the outer aqueous phase of the drug loading solution were removed, and the outer aqueous phase was replaced with the dialysis solution. A gemcitabine-contained liposome composition having a gemcitabine hydrochloride concentration of 0.54 mg/mL, an average particle diameter of 76.3 nm, an inner aqueous phase osmotic pressure of 1.039 mOsm/L, an outer aqueous phase osmotic pressure of 285 mOsm/L. and an osmotic pressure of an inner aqueous phase with respect to an outer aqueous phase of 3.6 times was obtained through the above-described step. The content ratio of the lysophospholipid contained in a lipid forming a liposome with respect to the total amount of phospholipids other than the lysophospholipid contained in the lipid forming the liposome is 0.62 mol %.

Example 2

A gemcitabine-contained liposome composition was prepared in the same manner as in the drug loading solution in Example 1 except that the solution was cooled to 40° C. within 5 minutes. The content ratio of the lysophospholipid contained in a lipid forming a liposome with respect to the total amount of phospholipids other than the lysophospholipid contained in the lipid forming the liposome is 0.65 mol %.

Test Example 1

Measurement of Leakage Ratio in Plasma

50 μL of a liposome composition obtained from Example 1 or 2 was diluted (volume) 20 times with mouse plasma and incubated at 37° C. for 24 hours, and 100 μL was collected at points in time of 0, 1, 4, 7, and 24 hours. Subsequently, centrifugal filtration was carried out using an ultrafiltration filter (AMICON ULTRA-0.5 with 10 kDa manufactured by Millipore) under the conditions of 7,400×g, for 30 minutes, and at 4° C. Gemcitabine contained in the collected filtrate was quantitatively determined through liquid chromatography/ultraviolet-visible absorbance detection, and the leakage ratio was calculated by the following equation.

Leakage ratio (%)=(concentration of gemcitabine in filtrate after unit time of incubation)×20÷concentration of gemcitabine contained in liposome composition×100   Equation:

The results of leakage ratio are shown in Table 1 and FIG. 1.

The lipid of the "Content ratio of lipid in liposome composition" in Table 1 also contains a lysophospholipid. The "Content ratio of lysophospholipid" in Table 1 means the content ratio of a lysophospholipid contained in a lipid forming a liposome with respect to the total amount of phospholipids other than the lysophospholipid contained in the lipid forming the liposome.

TABLE 1

|  | Example 1 | Example 2 |
|---|---|---|
| Average particle diameter (nm) | 77.5 | 73.2 |
| Gemcitabine concentration (mg/mL) | 0.59 | 0.67 |
| Content ratio (w/v %) of lipid in liposome composition | 1.55 | 1.98 |
| Gemcitabine/lipid ratio (w/w %) | 3.8 | 3.4 |
| Content ratio (mol %) of lysophospholipid | 0.62 | 0.65 |
| Leakage ratio (%) after 24 hours | 23 | 32 |

In all of the liposome compositions of Examples 1 and 2, the leakage rate was suppressed and favorable results were obtained, but the liposome composition of Example 1 showed better leakage rate (FIG. 1). The inclination of initial leakage within 4 hours is large in the liposome composition of Example 2, whereas the drug in the liposome composition of Example 1 leaks with a linear inclination. This suggests that the liposome composition of Example 2 contains nonuniform particles of a part of a liposome membrane, which bursts at an initial stage. In order to suppress side effects of the drug, it is preferable that the drug leaks at a constant rate, and the liposome composition of Example 1 is more preferable than the liposome composition of Example 2.

Test Example 2

Measurement of Particle Size Distribution

The liposome composition obtained in Example 1 or 2 was diluted 33 times the mass with phosphate-buffered physiological saline and measurement was performed through a dynamic light scattering method using FPAR-1000AS (manufactured by OTSUKA ELECTRONICS Co., LTD.)

The results are shown in Table 2.

In all of the liposome compositions of Examples 1 and 2, no liposome composition having a particle diameter of greater than or equal to 200 nm was detected, and a liposome composition which can be treated with a 0.2 μm filtration filter was obtained.

Example 3 a) Preparation of Oil Phase 16.6 g, 2.0 g, and 4.3 g of hydrogenated soybean phosphatidylcholine, cholesterol, and an N-(carbonyl-methoxy-polyethylene glycol 2000)-1,2-distearoyl-sn-glycero-3-phosphoethanolamine sodium salt (hereinafter, also referred to as DSPE-PEG) were respectively taken so as to have a molar ratio of 76/19/5. Subsequently, 406 mL of an organic solvent (ethanol/ethyl acetate=3/1) was added thereto and lipids are dissolved at a heated temperature of 70° C. to obtain an oil phase.

b) Preparation of Aqueous Phase

A 4 mM phosphate buffer solution was prepared and used as an aqueous phase.

c) Preparation of Drug Non-Contained Liposome

The aqueous phase was heated to 70° C. and the oil phase was added thereto so that the volume ratio of water phase/oil phase=8/3, and then, the aqueous phase and the oil phase were mixed using a rotary stirring emulsifier (M Technique Co., Ltd.) at a circumferential speed of 20 m/s at 13,000 rpm for 30 minutes. Thereafter, the organic solvent and water were evaporated by supplying nitrogen while heating the mixture to higher than or equal to a phase transition temperature, and the mixture was concentrated so as to became a volume of about 1/10 of the volume before emulsification, to obtain a drug non-contained liposome. The average particle diameter at this time was 67 nm.

d) Preparation of Drug-Contained Liposome

Gemcitabine hydrochloride was used as a drug. Gemcitabine hydrochloride was purchased from TEVA.

1) Preparation of PBS (10×)

82.01 g of sodium chloride, 14.42 g of disodium hydrogen phosphate dodecahydrate, and 2.30 g of sodium dihydrogen phosphate dihydrate were dissolved in 1,060.1 g of water for injection to prepare PBS (10×).

2) Preparation of Drug Loading Solution 0.0973 g of gemcitabine hydrochloride, 0.425 g of PBS, and 0.464 g of water for injection of Japanese Pharmacopoeia were mixed with each other and were dissolved at 45° C. to 70° C. to prepare a drug solution. The temperature of this drug solution was kept at 45° C., 1.1 mL of a drug non-encapsulated liposome and 8 M sodium hydroxide were added thereto, and the pH was adjusted to 5.0. Next, the solution was heated at 70° C. for 10 minutes, and then, cooled to 40° C. over 30 minutes and diluted with a 1.016 mM sucrose/37 mM histidine solution. A 275 mM sucrose/10 mM histidine aqueous solution was prepared as an obtained dialysis solution of the liposome composition through dialysis. The osmotic pressure obtained from the solute molarity of this solution was 285 mOsm/L. Dialysis was performed at room temperature using this dialysis solution, each solute and non-encapsulated gemcitabine hydrochloride present in the outer aqueous phase of the drug loading solution were removed, and the outer aqueous phase was replaced with the dialysis solution. A gemcitabine-contained liposome composition having a gemcitabine hydrochloride concentration of 0.68 mg/mL and a lipid content ratio of 2.0 w/v % in the liposome composition was obtained through the above-described step. The content ratio of the lysophospholipid contained in a lipid forming a liposome with respect to the total amount of phospholipids other than the lysophospholipid contained in the lipid forming the liposome is 1.0 mol %.

Example 4

A gemcitabine-contained liposome composition was prepared in the same manner as in the drug loading solution in Example 3 except that the pH was adjusted to 7.3. A gemcitabine-contained liposome composition having a gemcitabine hydrochloride concentration of 0.79 mg/mL and a lipid content ratio of 2.0 w/v % in the liposome composition was obtained. The content ratio of the lysophospholipid contained in a lipid forming a liposome with respect to the total amount of phospholipids other than the lysophospholipid contained in the lipid forming the liposome is 0.6 mol %.

Example 5

A gemcitabine-contained liposome composition was prepared in the same manner as in the drug loading solution in Example 3 except that the pH was adjusted to 9.4. A gemcitabine-contained liposome composition having a gemcitabine hydrochloride concentration of 0.67 mg/mL and a lipid content ratio of 2.1 w/v % in the liposome composition was obtained. The content ratio of the lysophospholipid contained in a lipid forming a liposome with respect to the total amount of phospholipids other than the lysophospholipid contained in the lipid forming the liposome is 2.2 mol %.

Comparative Example 1

A gemcitabine-contained liposome composition was prepared in the same manner as in the drug loading solution in Example 3 except that the pH was adjusted to 3.9. A gemcitabine-contained liposome composition having a gemcitabine hydrochloride concentration of 0.42 mg/mL and a lipid content ratio of 2.3 w/v % in the liposome composition was obtained. The content ratio of the lysophospholipid contained in a lipid forming a liposome with respect to the total amount of phospholipids other than the lysophospholipid contained in the lipid forming the liposome is 3.7 mol %.

The gemcitabine/lipid ratios of Examples 3 to 5 and Comparative Example 1 are shown in Table 2.

TABLE 2

| | Comparative Example 1 | Example 3 | Example 4 | Example 5 |
|---|---|---|---|---|
| pH | 3.9 | 5.0 | 7.3 | 9.4 |
| Gemcitabine concentration (mg/mL) | 0.42 | 0.68 | 0.79 | 0.67 |
| Content ratio (w/v %) of lipid in liposome composition | 2.3 | 2.0 | 2.0 | 2.1 |
| Gemcitabine/lipid ratio (w/w %) | 1.8 | 3.4 | 4.0 | 3.3 |
| Content ratio (mol %) of lysophospholipid | 3.7 | 1.0 | 0.6 | 2.2 |

In the drug loading, a favorable gemcitabine/lipid ratio is shown which is obtained by performing the step of heating the mixture to a temperature higher than or equal to 55° C. at a pH of 5.0 to 13, preferably at a pH of 6.0 to 9.0, and more preferably at a pH of 6.5 to 8.0. This suggests that the production of lysophospholipids is suppressed and an excellent leakage rate is shown.

What is claimed is:

1. A method of producing a liposome composition, the method comprising the following steps:
   (a) preparing empty liposomes by an O/W type emulsification of an oil phase, wherein said oil phase comprises hydrogenated soybean phosphatidylcholine, cholesterol, and 1,2-distearoyl-3-phosphatidylethanolamine-polyethlene glycol dissolved in an organic solvent, and an aqueous phase having pH 5-9, and removing the organic solvent after forming the empty liposomes;
   (b) preparing a drug solution by dissolving gemcitabine or a salt thereof at pH 1-5;
   (c) mixing the empty liposomes and the drug solution;
   (d) adjusting pH with a pH adjuster; and
   (e) heating to 55° C. or higher at pH 5.0 to 13,
   wherein the liposome composition comprises liposomes which encapsulate gemcitabine or a salt thereof, wherein a lipid forming the liposomes comprises hydrogenated soybean phosphatidylcholine, cholesterol, 1,2-distearoyl-3-phosphatidylethanolamine-polyethlene glycol and a lysophospholipid produced by hydrolysis of hydrogenated soybean phosphatidylcholine,
   a content ratio of gemcitabine or a salt thereof to the lipid is 2 mass % to 10 mass %, and
   a content ratio of the lysophospholipid contained in the lipid forming the liposomes with respect to a total amount of hydrogenated soybean phosphatidylcholine contained in the liposomes is 0.01 mol % to 3 mol %.

2. The method of producing the liposome composition according to claim 1, wherein a content ratio of cholesterol with respect to a total amount of all lipids forming the liposomes is 10 mol % to 35 mol %.

3. The method according to claim 2, wherein the organic solvent is a mixed solvent of water-soluble and ester-based organic solvents and is substantially free of organic solvents such as chloroform, methylene chloride, hexane, and cyclohexane.

4. The method of producing the liposome composition according to claim 1, wherein a content ratio of cholesterol with respect to a total amount of all lipids forming the liposomes is 17 mol % to 35 mol %.

5. The method according to claim 4, wherein the organic solvent is a mixed solvent of water-soluble and ester-based organic solvents and is substantially free of organic solvents such as chloroform, methylene chloride, hexane, and cyclohexane.

6. The method according to claim 1, wherein the organic solvent is a mixed solvent of water-soluble and ester-based organic solvents and is substantially free of organic solvents such as chloroform, methylene chloride, hexane, and cyclohexane.

* * * * *